(12) United States Patent
Kawase et al.

(10) Patent No.: US 11,235,170 B2
(45) Date of Patent: Feb. 1, 2022

(54) PHOTOTHERAPEUTIC APPARATUS

(71) Applicant: Teijin Pharma Limited, Tokyo (JP)

(72) Inventors: Yuki Kawase, Tokyo (JP); Takamitsu Okayama, Tokyo (JP); Daisuke Niwa, Tokyo (JP); Rei Tamiya, Tokyo (JP); Shosaku Motohara, Tokyo (JP); Satoshi Igarashi, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 53 days.

(21) Appl. No.: 16/617,194

(22) PCT Filed: May 21, 2018

(86) PCT No.: PCT/JP2018/019441
§ 371 (c)(1),
(2) Date: Nov. 26, 2019

(87) PCT Pub. No.: WO2018/221284
PCT Pub. Date: Dec. 6, 2018

(65) Prior Publication Data
US 2021/0121712 A1    Apr. 29, 2021

(30) Foreign Application Priority Data
May 31, 2017   (JP) .............................. JP2017-107907

(51) Int. Cl.
*A61N 5/06* (2006.01)

(52) U.S. Cl.
CPC .... *A61N 5/0622* (2013.01); *A61N 2005/0626* (2013.01); *A61N 2005/0633* (2013.01); *A61N 2005/0645* (2013.01)

(58) Field of Classification Search
CPC .......... A61N 5/0622; A61N 2005/0633; A61N 2005/0645; A61N 2005/0626
See application file for complete search history.

(56) References Cited

U.S. PATENT DOCUMENTS

| 2005/0269473 | A1* | 12/2005 | Carnevali | .............. G06K 7/109 248/311.2 |
| 2007/0156208 | A1* | 7/2007 | Havell | ................. A61N 5/0616 607/88 |

(Continued)

FOREIGN PATENT DOCUMENTS

| CN | 101677835 A | 3/2010 |
| CN | 104349751 A | 2/2015 |

(Continued)

OTHER PUBLICATIONS

International Search Report for PCT/JP2018/019441, dated Aug. 21, 2018 [PCT/ISA/210].

(Continued)

*Primary Examiner* — Brian T Gedeon
*Assistant Examiner* — Joshua Andrew Schum-Houck
(74) *Attorney, Agent, or Firm* — Sughrue Mion, PLLC

(57) ABSTRACT

A phototherapy device including: an irradiation probe for radiating irradiation light toward a living body; a probe fixing unit into which the irradiation probe is inserted and at the same time fixed on a living body; an observation module placed on the probe fixing unit and provided with an observation means for observing an irradiation site irradiated with irradiation light which is radiated to the living body; and a moving means capable of moving the observation module to a space where the irradiation probe is to be placed in the probe fixing unit during observation of the irradiation site.

12 Claims, 13 Drawing Sheets

(56) References Cited

U.S. PATENT DOCUMENTS

| | | | |
|---|---|---|---|
| 2011/0190741 A1 | 8/2011 | Deisinger et al. | |
| 2013/0137992 A1* | 5/2013 | Yamazaki | A61N 5/0619 |
| | | | 600/476 |
| 2015/0162109 A1* | 6/2015 | Nager | A61K 41/0052 |
| | | | 606/27 |
| 2016/0022118 A1 | 1/2016 | Dejima | |
| 2016/0106999 A1* | 4/2016 | Michaels | A61M 37/00 |
| | | | 604/20 |
| 2016/0243378 A1* | 8/2016 | Van Der Zaan-Landwehr Johan | A61N 5/0616 |

FOREIGN PATENT DOCUMENTS

| | | |
|---|---|---|
| CN | 204562371 U | 8/2015 |
| CN | 104939921 A | 9/2015 |
| CN | 105163663 A | 12/2015 |
| CN | 105879245 A | 8/2016 |
| CN | 205494696 U | 8/2016 |
| EP | 1173104 A1 | 1/2002 |
| EP | 2599469 A1 | 6/2013 |
| JP | 2009-172068 A | 8/2009 |
| JP | 2012-500677 A | 1/2012 |
| JP | 5739888 B2 | 6/2015 |
| JP | 2015-198743 A | 11/2015 |
| KR | 10-1589737 B1 | 1/2016 |
| KR | 10-2016-0035153 A | 3/2016 |
| KR | 10-2016-0093584 A | 8/2016 |
| WO | 00/59395 A1 | 10/2000 |
| WO | WO-2009117323 A2 * | 9/2009 ........... A61N 5/0622 |
| WO | 2014/157473 A1 | 10/2014 |
| WO | 2016/025915 A1 | 2/2016 |

OTHER PUBLICATIONS

Written Opinion for PCT/JP2018/019441, dated Aug. 21, 2018 [PCT/ISA/237].

Communication, dated Feb. 17, 2020, issued by the European Patent Office in counterpart European Application No. EP 18 81 0824.

Communication dated Apr. 13, 2021 from the China National Intellectual Property Administration in CN Application No. 201880036040.8, 27 pages with translation.

* cited by examiner

[Fig. 1]
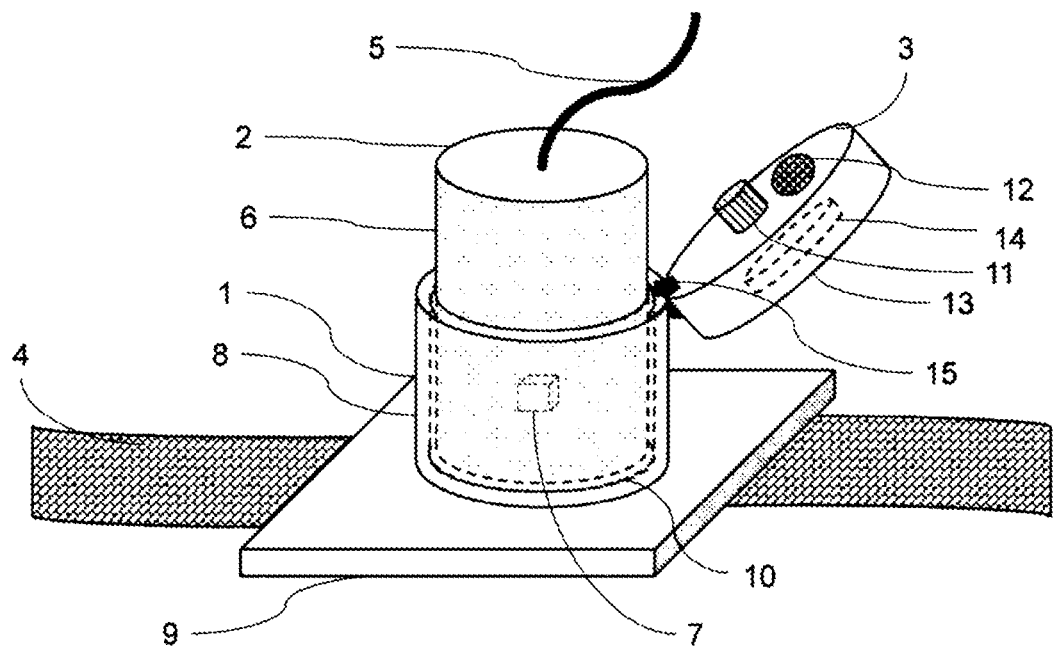
[Fig. 2]
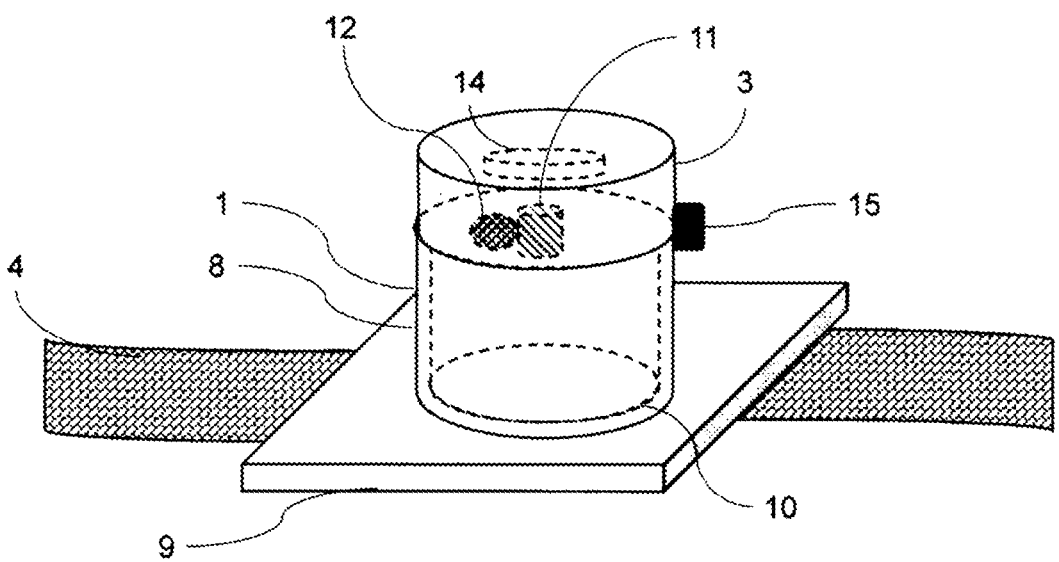

[Fig. 3]
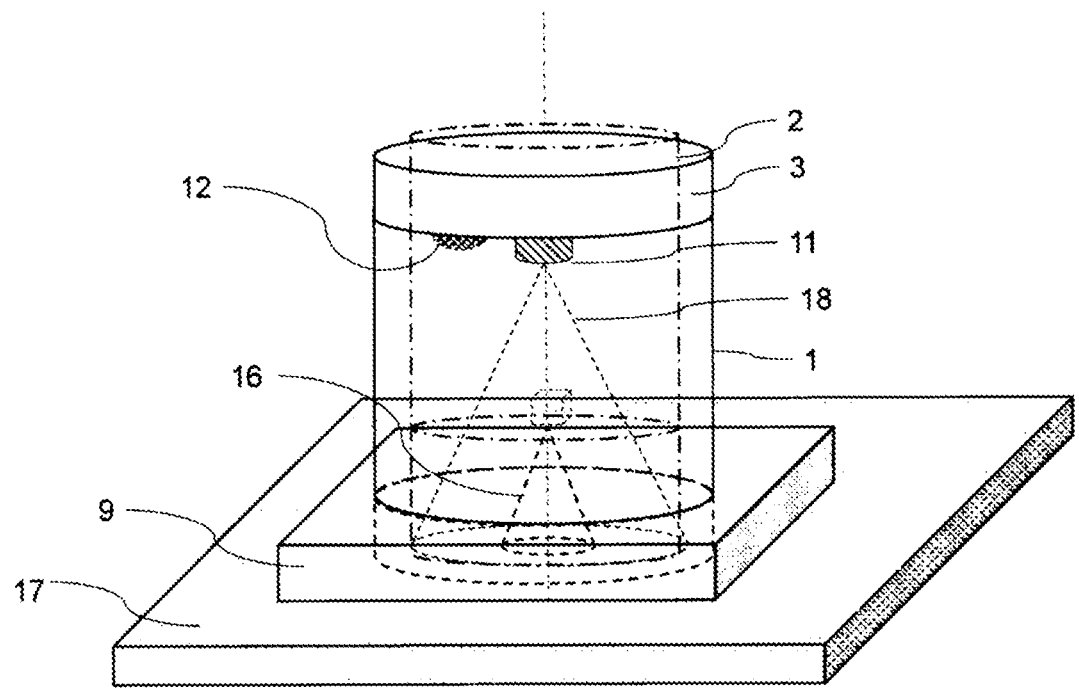
[Fig. 4]
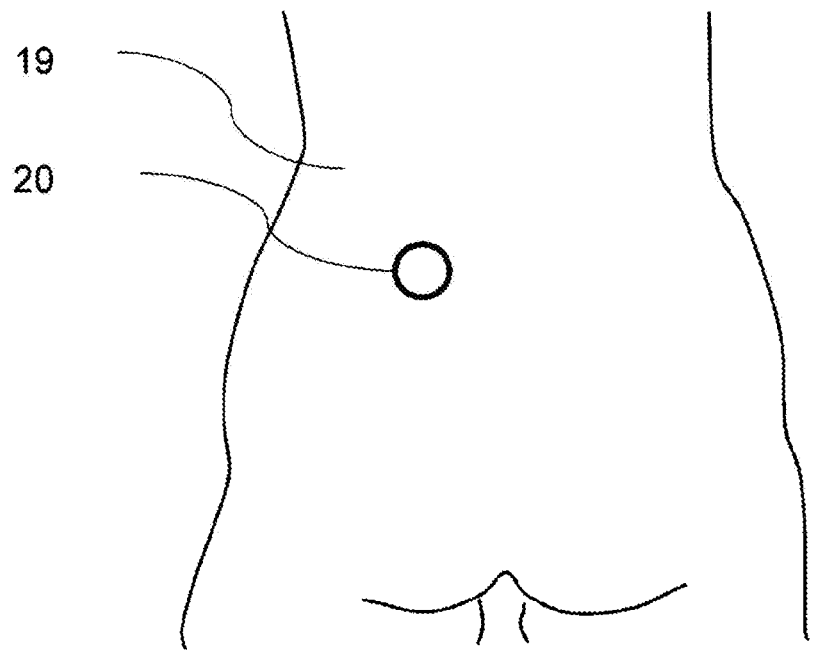

[Fig. 5]
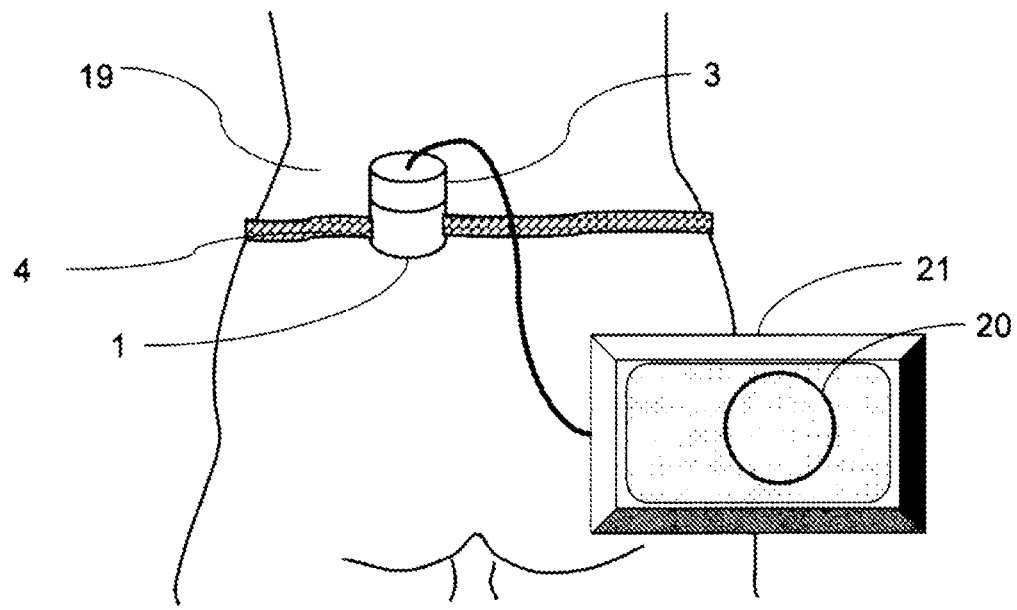
[Fig. 6]
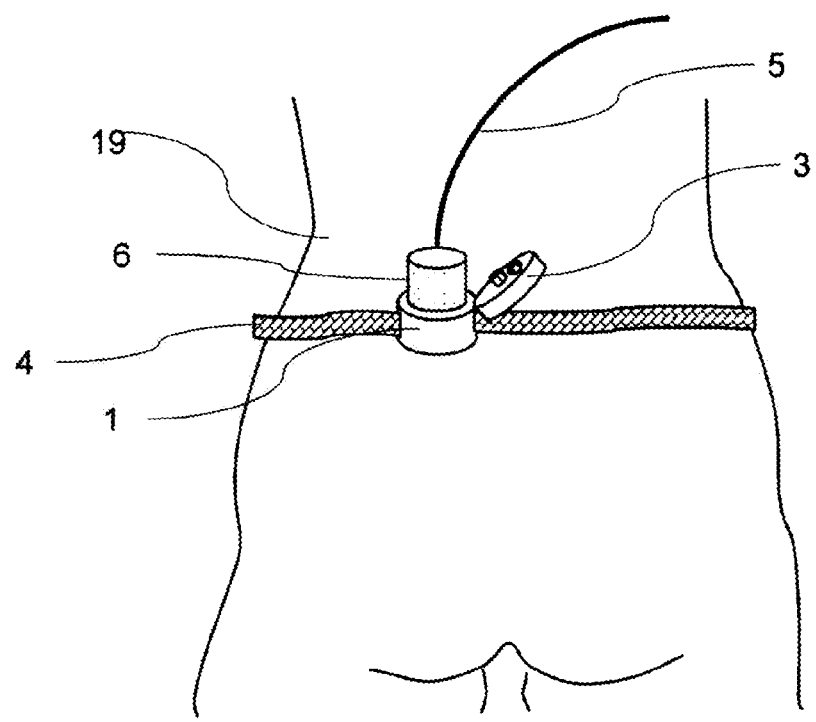

[Fig. 7]
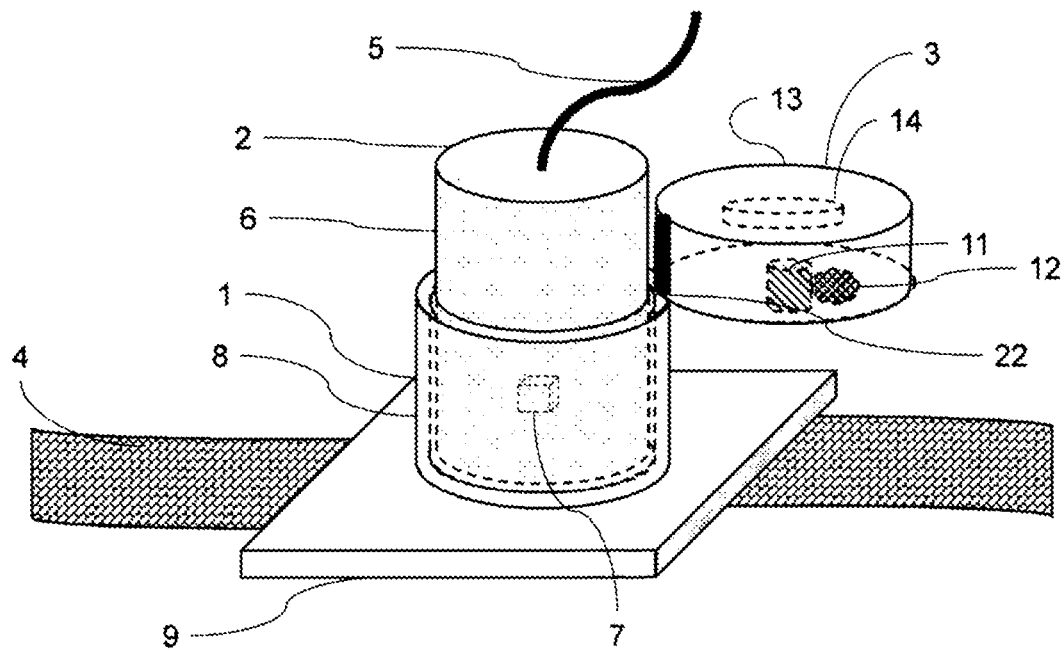
[Fig. 8]
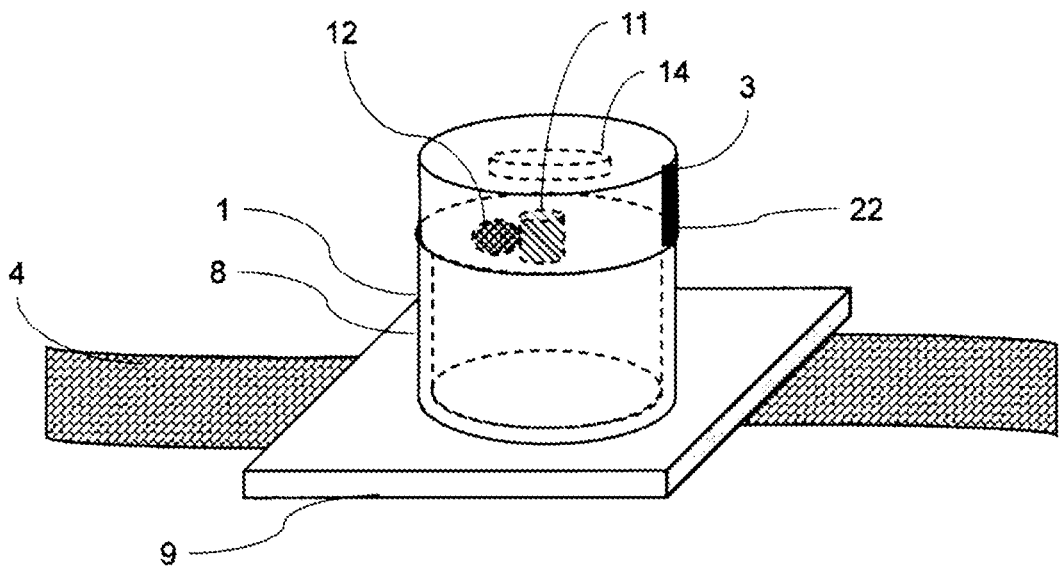

[Fig. 9]
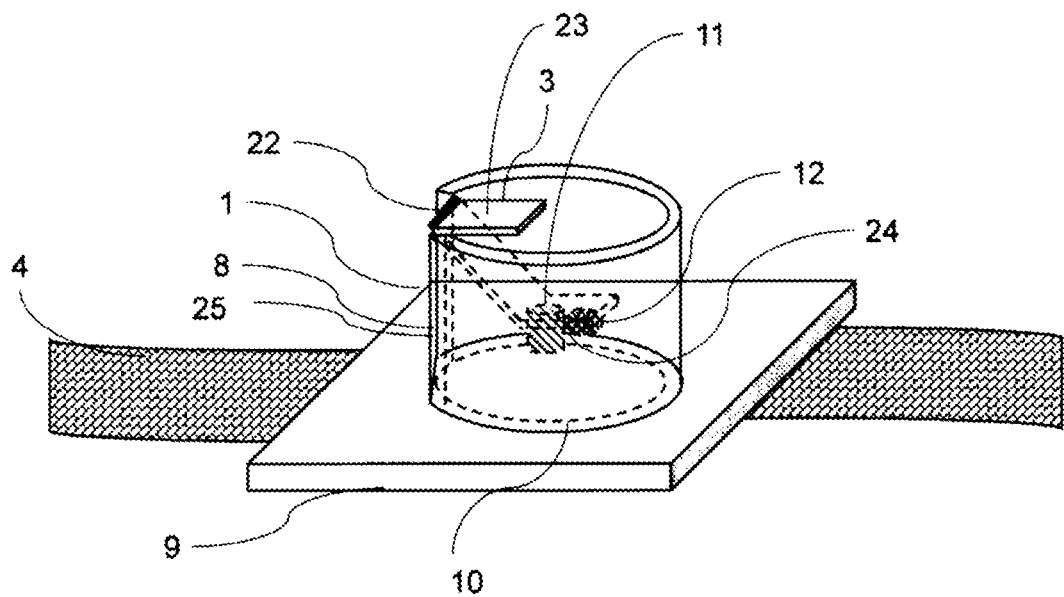
[Fig. 10]
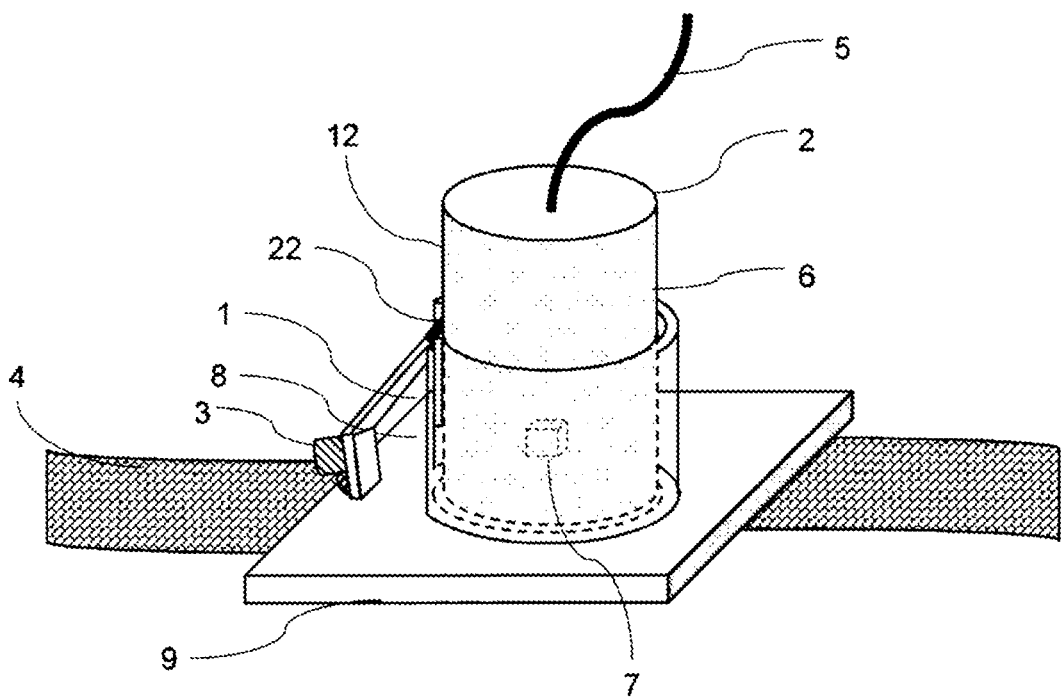

[Fig. 11]
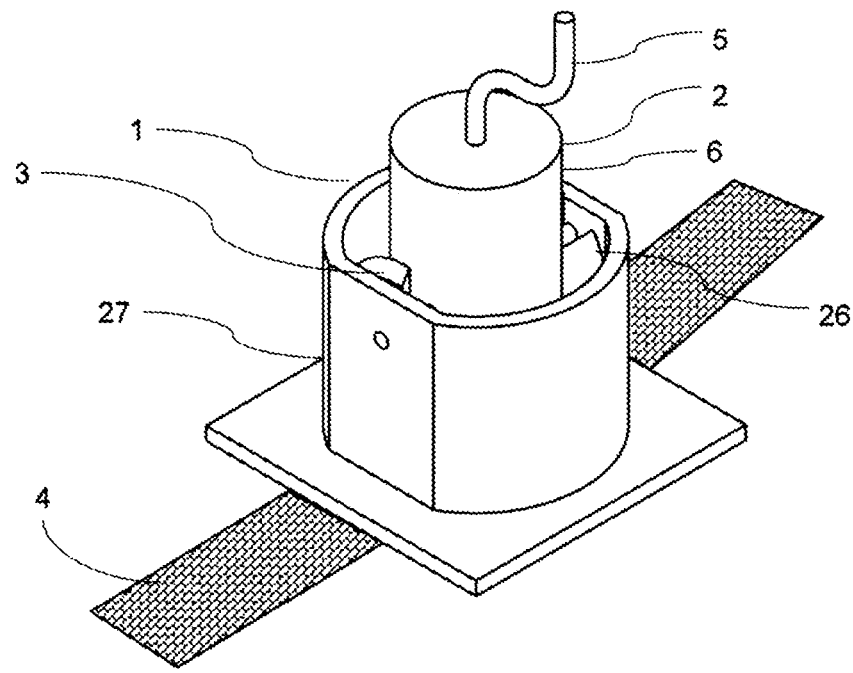
[Fig. 12]
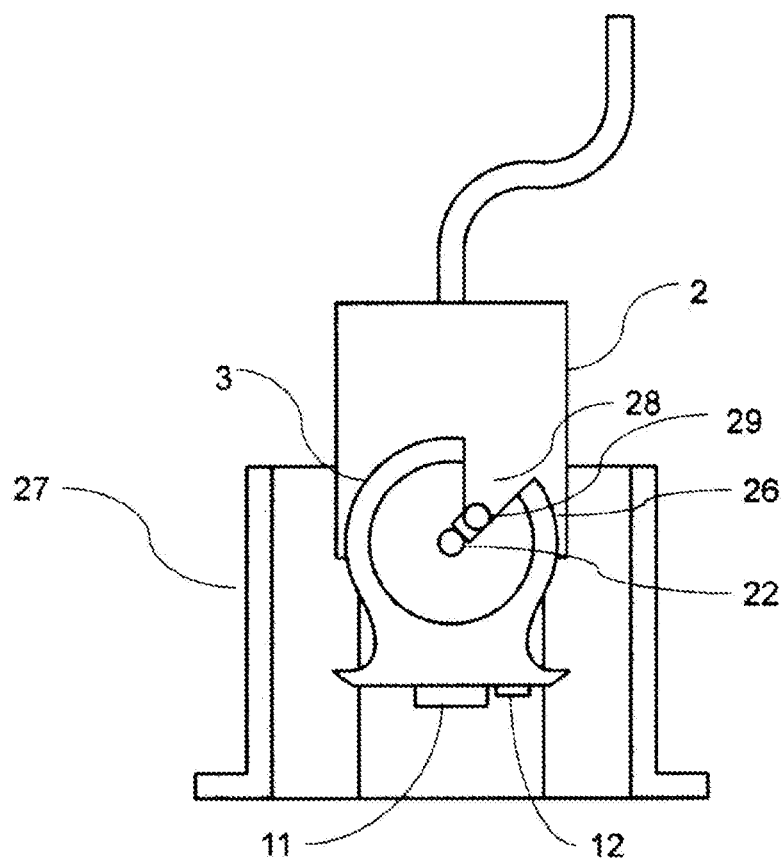

[Fig. 13]
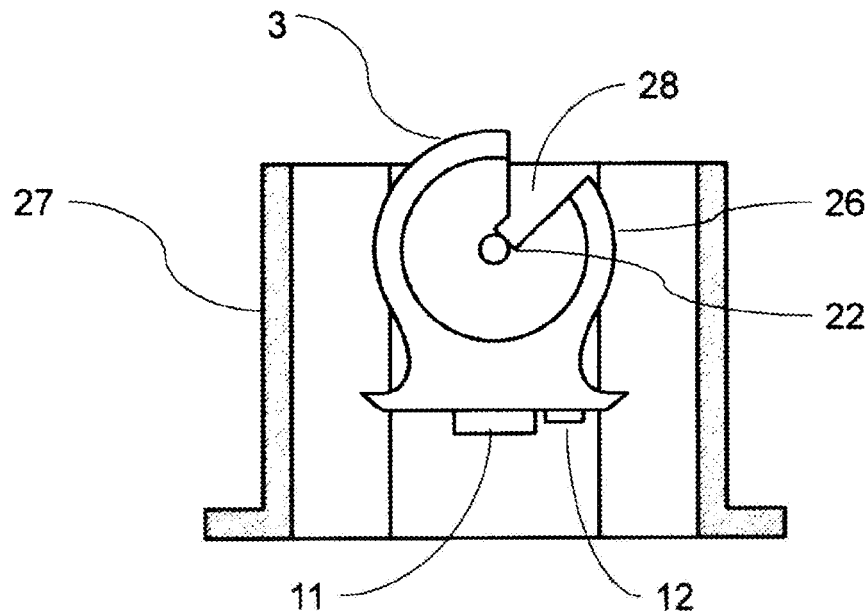
[Fig. 14]
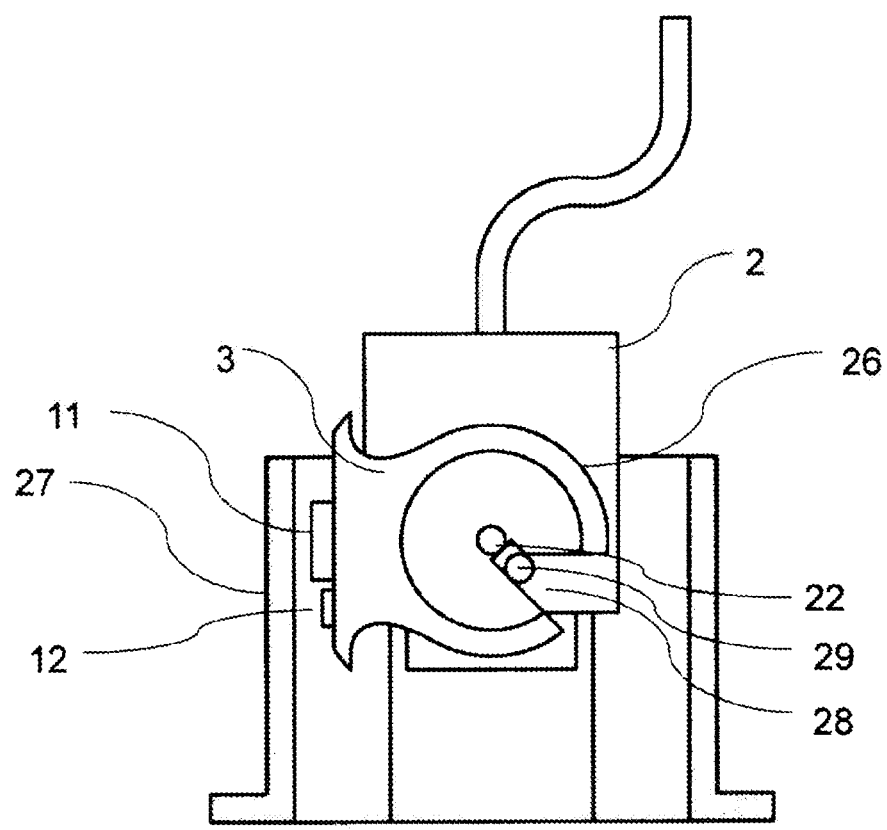

[Fig. 15]
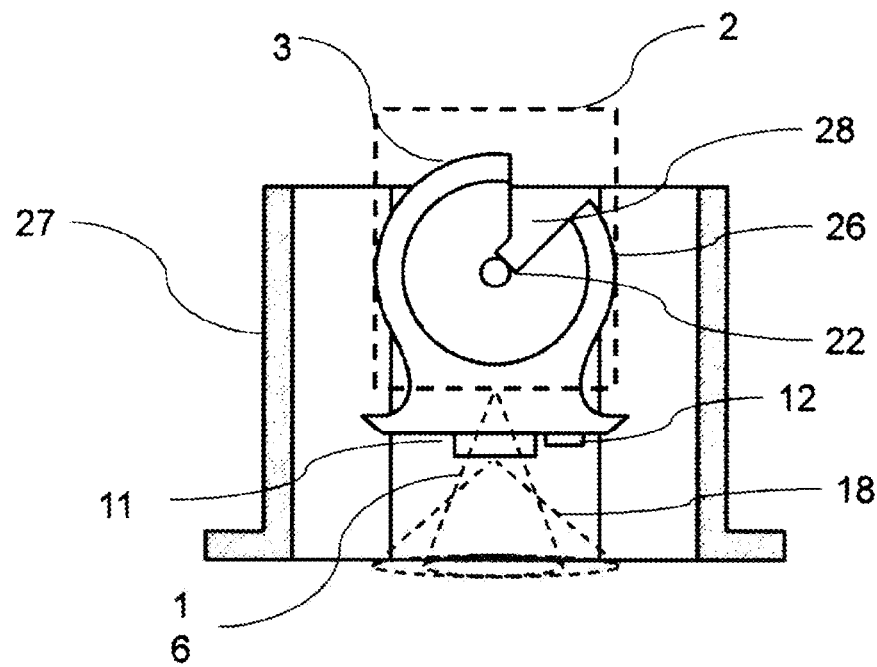
[Fig. 16]
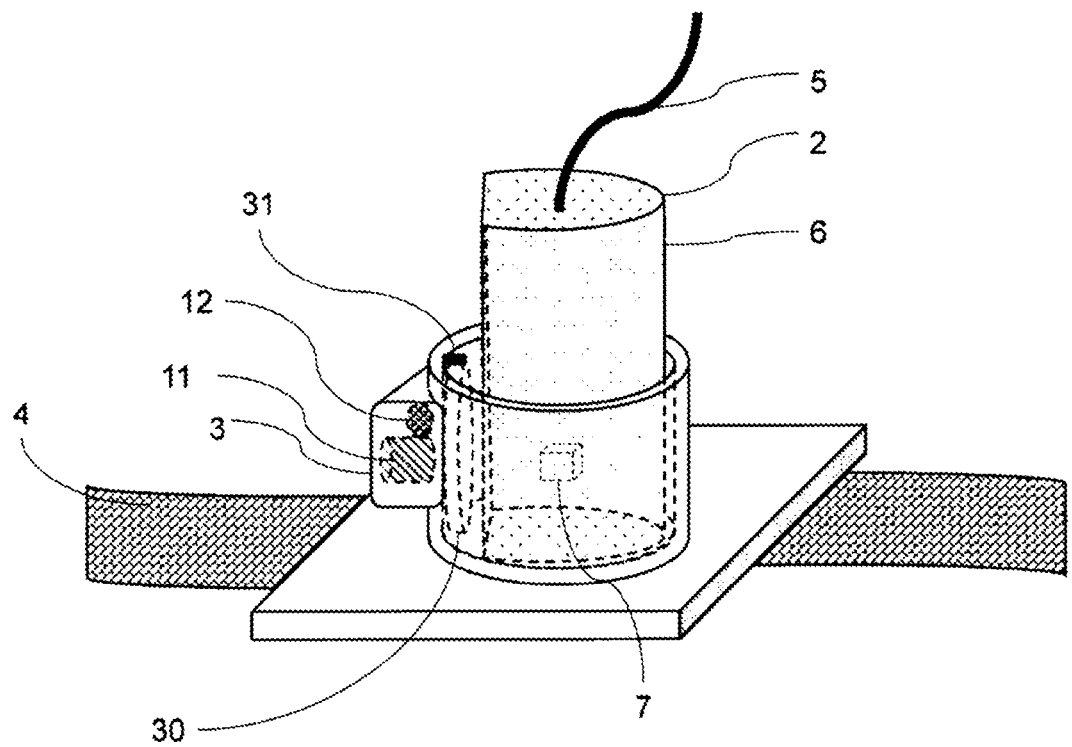

[Fig. 17]
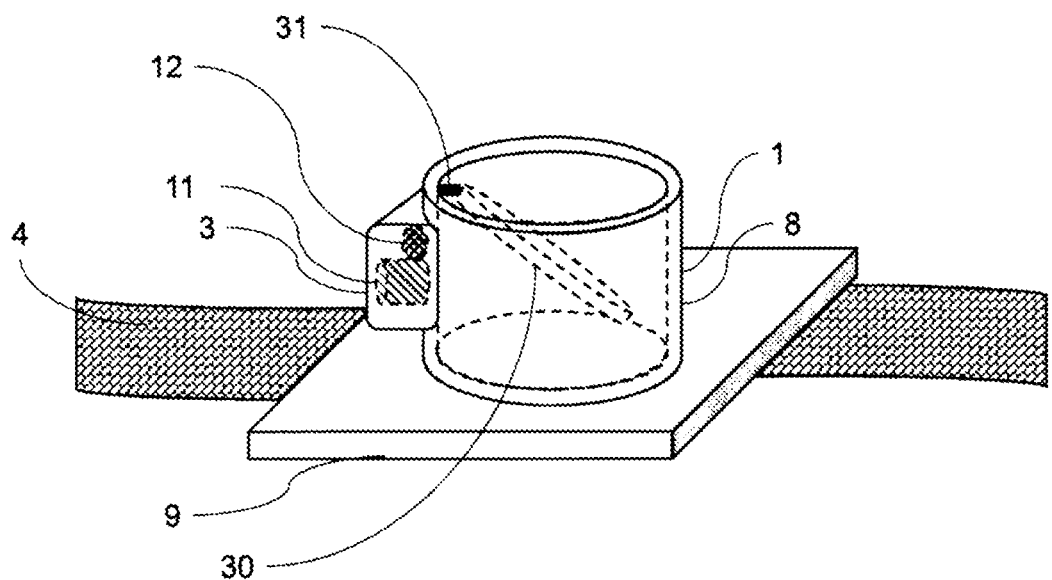
[Fig. 18]
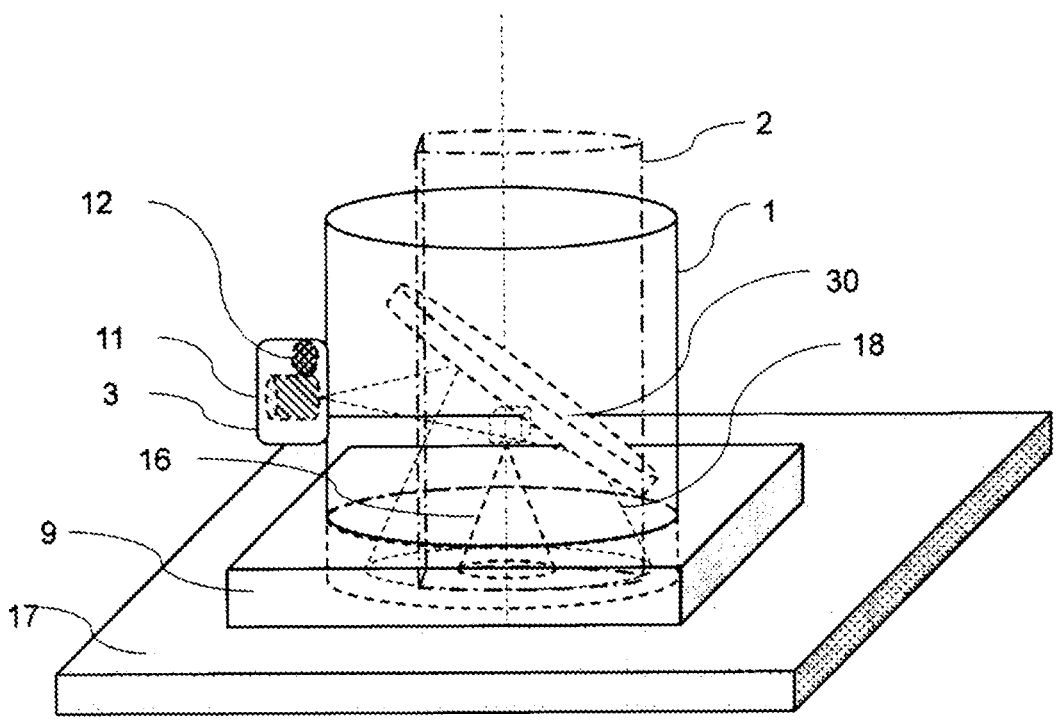

[Fig. 19]
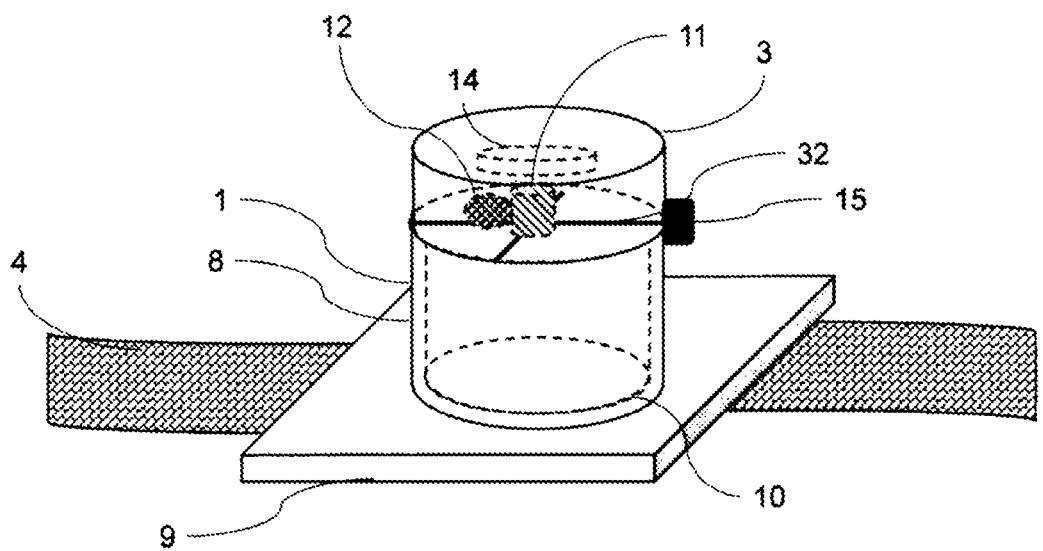
[Fig. 20]
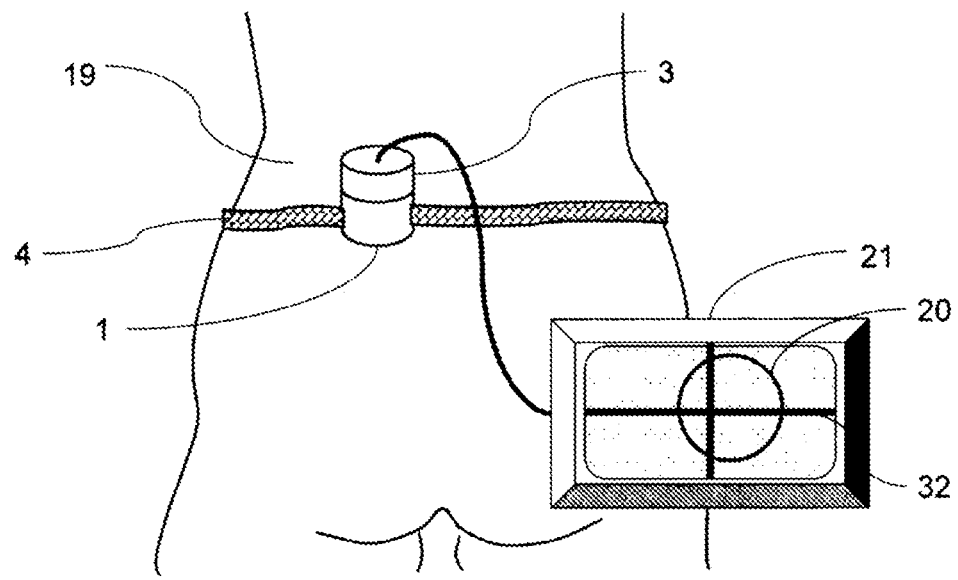

[Fig. 21]
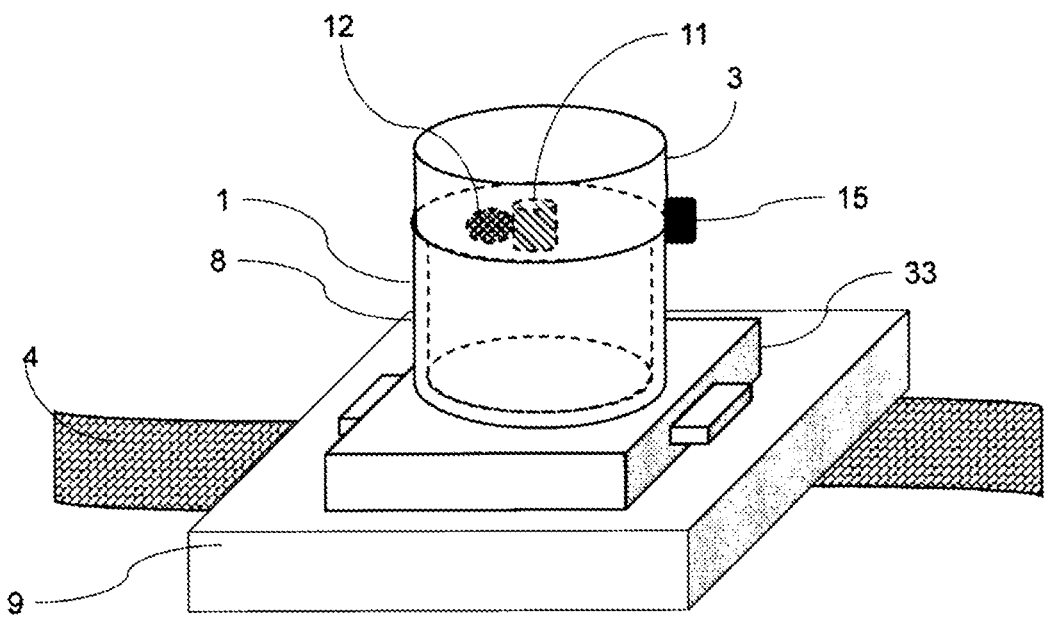
[Fig. 22]
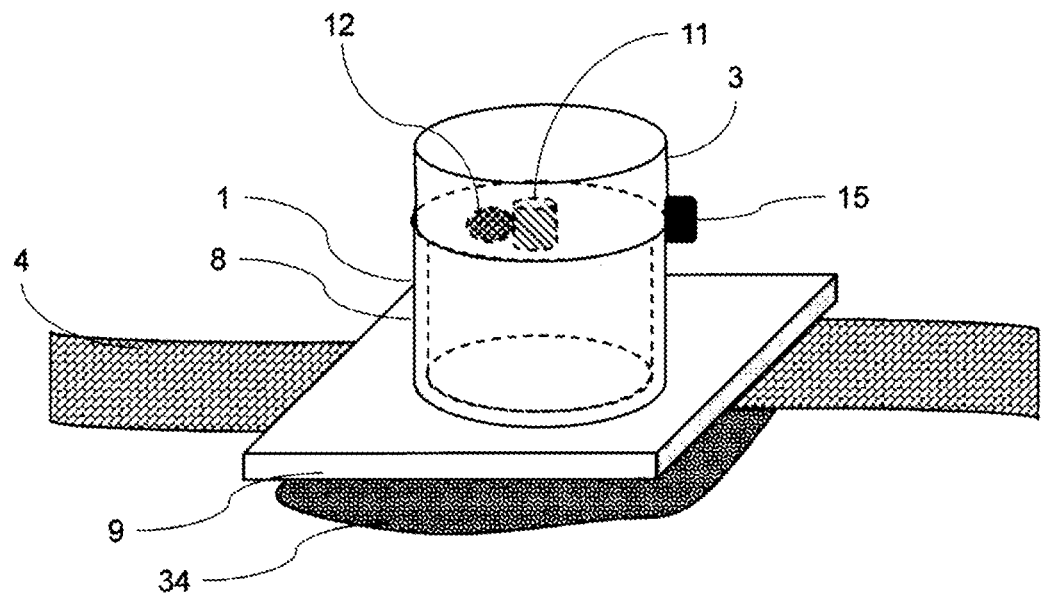

[Fig. 23]
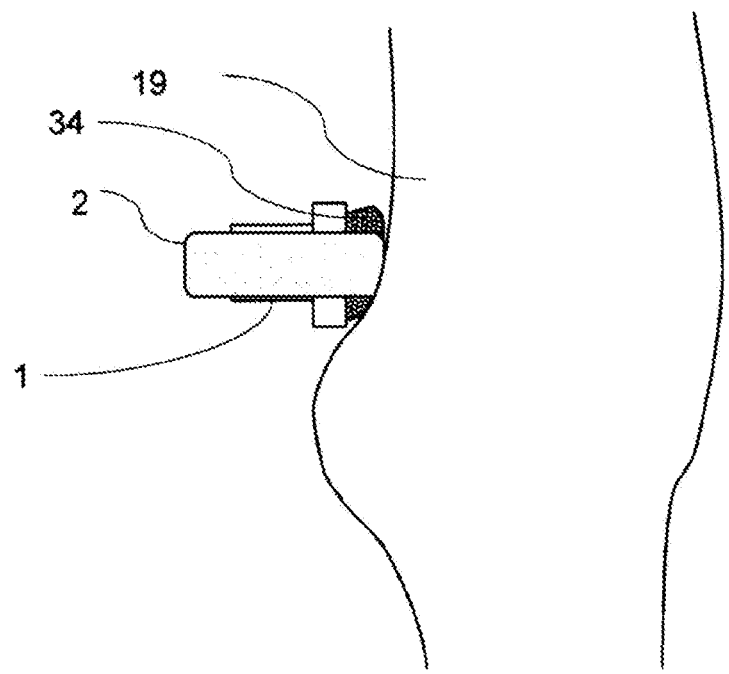
[Fig. 24]
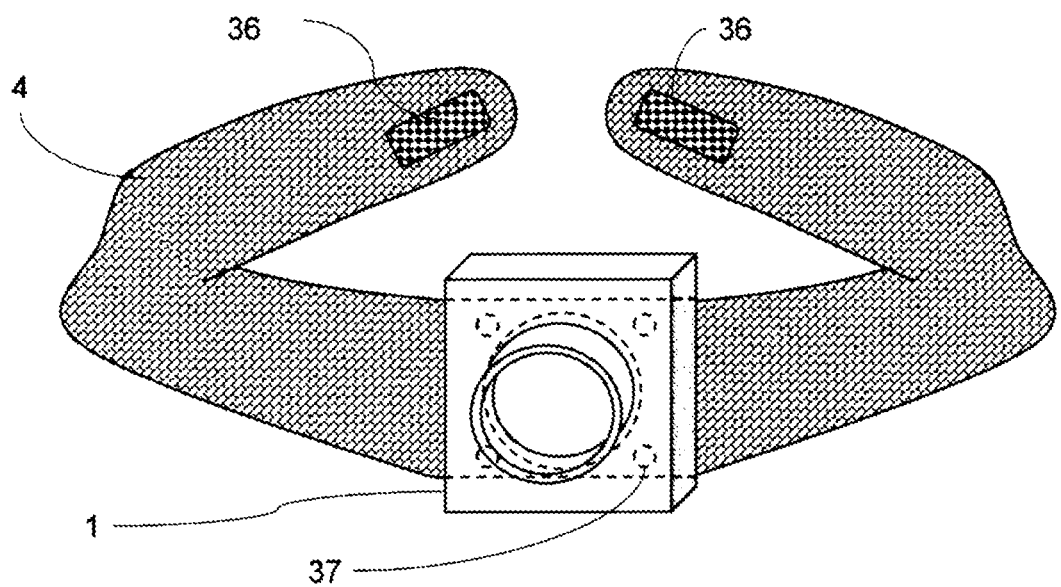

[Fig. 25]
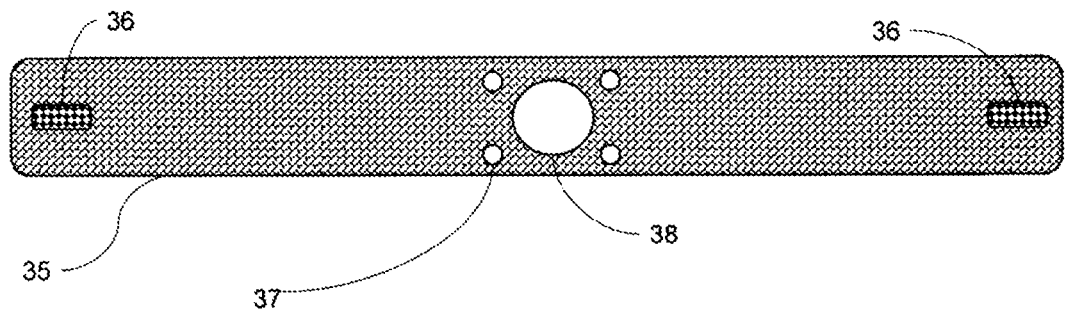
[Fig. 26]
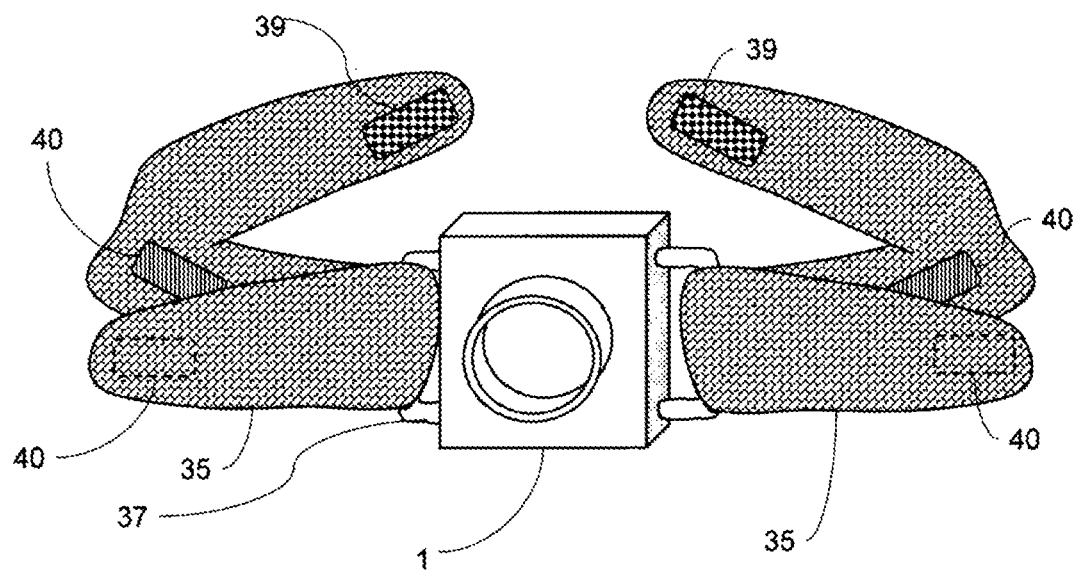
[Fig. 27]
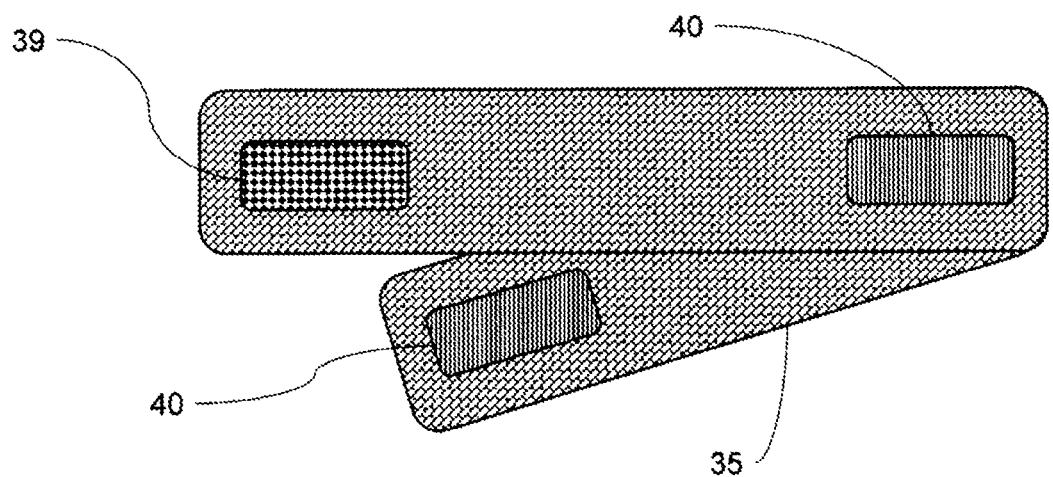

PHOTOTHERAPEUTIC APPARATUS

CROSS REFERENCE TO RELATED APPLICATIONS

This application is a National Stage of International Application No. PCT/JP2018/019441 filed May 21, 2018, claiming priority based on Japanese Patent Application No. 2017-107907 filed May 31, 2017.

TECHNICAL FIELD

The present invention relates to a phototherapy device.

BACKGROUND ART

Phototherapy devices have been used for treatment such as relief of aching pain by irradiating an affected area or an acupressure point, for example, with infrared light (approximate wavelengths of 700 nm to 2500 nm) as treatment light percutaneously. It has recently been revealed that irradiation of light has an action on various nerves, such as selective suppression of nerve conduction in sensory fibers that transmit pain in peripheral nervous system, suppression of pain-producing substances, relief of sympathicotonia and the like. These actions have been applied to improve and treat lower urinary tract symptoms (LUTS) by photoirradiation (PLT 1). Among lights, laser light is widely used in these applications since it can be radiated at a specific wavelength with high power. In such treatment, the same site such as an affected area and an acupoint is repeatedly irradiated, and it is necessary to promptly specify a treatment site. For this reason, for example, PLT 2 proposes a configuration including image-taking means of taking an image of a site to be irradiated with laser light in addition to a laser light source means of radiating laser light into a photoirradiation probe. With this configuration, the image-taking means takes pictures to provide rough understanding of the state and the position of the affected area.

CITATION LIST

Patent Literatures

[PTL 1] Japanese Unexamined Patent Application Publication No. 2009-172068
[PTL 2] Japanese Patent No. 5739888

SUMMARY OF INVENTION

Technical Problem

For example, in LUTS treatment by photoirradiation, the sacral foramina where bladder sensory nerves exist is aimed at and irradiated with light percutaneously in order to suppress abnormal activities of sensory nerves in the bladder. It is necessary to accurately aim at the sacral foramina for appropriate treatment. Photoirradiation is preferably performed by the patient himself/herself at home since photoirradiation for a few minutes to tens of minutes per day need to be repeated at a frequency of twice a week to every day. For this, the physician locates the sacral foramina at hospital and places a marking indicating the irradiation position and the irradiation area on the skin just over the sacral foramina. The patient then performs photoirradiation at home with the help of the mark. The sacral foramina is positioned under the skin slightly below the lumbar region and in the back where the marking placed on the skin is out of sight of the patient. For this reason, positioning using imaging means such as a camera is necessary.

Adjusting the irradiation probe to aim the irradiation position on the back and keeping the irradiation probe at the adjusted position force the patient to take a strained posture. In this case, therefore, using the method of positioning the irradiation probe relative to the marking on the patient with the camera equipped in the irradiation probe as disclosed in PLT 2 leads to increasing a burden on the patient.

In this respect, when this treatment is carried out at home, a probe fixing unit which inserts and fixes the irradiation probe toward the patient may be used to position the probe fixing unit appropriately relative to the patient's marking in advance. However, when a camera is equipped in the probe fixing unit and the camera is placed such that the marking is captured by the camera in the appropriately positioned state, the irradiation probe may interfere with the camera when being inserted into the probe fixing unit. This problem is conspicuous particularly when the camera is disposed such that the optical axis of the camera is present coaxially relative to the optical axis of the light source of the irradiation probe fixed in the probe fixing unit in order to improve the positioning accuracy.

An object of the present invention is therefore to provide a phototherapy device that enables photoirradiation accurately aiming at the sacral foramina and consequently provides appropriate treatment even when the treatment site is in the back which is out of sight of the patient, and the patient himself/herself performs photoirradiation at home, for example, as is the case of photoirradiation for LUTS patients.

Solution to Problem

In order to achieve the object, a phototherapy device of the present invention includes an irradiation probe for radiating irradiation light toward a living body, a probe fixing unit into which the irradiation probe is inserted and at the same time fixed on a living body, an observation module placed on the probe fixing unit and provided with an observation means for observing an irradiation site irradiated with irradiation light which is radiated toward the living body, and a moving means capable of moving the observation module to a space where the irradiation probe is to be placed/inserted in the probe fixing unit during observation of the irradiation site.

Advantageous Effects of Invention

According to this configuration, even when the treatment site is in the back which is out of sight of the patient, and the patient performs photoirradiation by himself/herself, for example, at home, the patient himself/herself can perform positioning easily and fixing the irradiation probe on the back. Accordingly, this configuration enables photoirradiation accurately aiming at the sacral foramina and consequently provides appropriate treatment.

BRIEF DESCRIPTION OF DRAWINGS

FIG. 1 is a perspective view of an embodiment of the present phototherapy device.
FIG. 2 is a perspective view of an embodiment of the present phototherapy device.

FIG. 3 is a perspective view illustrating the positional relationship between irradiation light and the field of observation in the present phototherapy device.

FIG. 4 illustrates a state of use of the present phototherapy device.

FIG. 5 illustrates a state of use of the present phototherapy device.

FIG. 6 illustrates a state of use of the present phototherapy device.

FIG. 7 illustrates another embodiment of the present phototherapy device.

FIG. 8 illustrates another embodiment of the present phototherapy device.

FIG. 9 illustrates another embodiment of the present phototherapy device.

FIG. 10 illustrates another embodiment of the present phototherapy device.

FIG. 11 illustrates another embodiment of the present phototherapy device.

FIG. 12 illustrates another embodiment of the present phototherapy device.

FIG. 13 illustrates another embodiment of the present phototherapy device.

FIG. 14 illustrates another embodiment of the present phototherapy device.

FIG. 15 is a perspective view illustrating the positional relationship between the irradiation field and the field of observation in another embodiment of the present phototherapy device.

FIG. 16 illustrates another embodiment of the present phototherapy device.

FIG. 17 illustrates another embodiment of the present phototherapy device.

FIG. 18 is a perspective view illustrating the positional relationship between the irradiation field and the field of observation in another embodiment of the present phototherapy device.

FIG. 19 illustrates another embodiment of the present phototherapy device.

FIG. 20 illustrates another embodiment of the present phototherapy device.

FIG. 21 illustrates another embodiment of the present phototherapy device.

FIG. 22 illustrates another embodiment of the present phototherapy device.

FIG. 23 illustrates a state of use in another embodiment of the present phototherapy device.

FIG. 24 illustrates another embodiment of the present phototherapy device.

FIG. 25 illustrates another embodiment of the present phototherapy device.

FIG. 26 illustrates another embodiment of the present phototherapy device.

FIG. 27 illustrates another embodiment of the present phototherapy device.

DESCRIPTION OF EMBODIMENTS

Hardware Configuration of First Embodiment

A phototherapy device according to an embodiment of the present invention will be described below with reference to the accompanying drawings. The phototherapy device of the present embodiment is a device for performing LUTS treatment by irradiating the position of sacral foramina of the patient with light.

FIG. 1 is a perspective view of the phototherapy device according to the present embodiment with an irradiation probe 2 inserted in a probe fixing unit 1. The phototherapy device includes the irradiation probe 2, the probe fixing unit 1, an observation module 3, and a fixing belt 4.

The irradiation probe 2 is a member fixed to the probe fixing unit 1 for irradiating a predetermined irradiation site on the patient's skin with light. The irradiation probe 2 includes a probe cable 5 and a probe casing 6 and a treatment light source 7 is housed in the probe casing 6. Examples of the treatment light source 7 include a laser, an LED, a halogen lamp, or a xenon lamp. The treatment light source 7 is connected to a power supply for the treatment light source and a switch, which are not illustrated, through the probe cable 5, and the switch is operated to radiate light to the patient. As for the treatment light source 7, light may be externally guided into the probe casing 6 through a waveguide such as an optical fiber.

The probe casing 6 is formed of, for example, plastic or metal in a hollow cylindrical shape. The shape of the probe casing 6 is not necessarily cylindrical.

The probe fixing unit 1 includes a probe insertion part 8 and a patient contact part 9. The probe insertion part 8 is a member for fixing the irradiation probe 2 in the probe fixing unit 1 toward the patient by inserting the probe casing 6 therein.

The patient contact part 9 is a member for fixing the probe fixing unit 1 to the patient's body surface to irradiate the irradiation site on the patient's body surface with light from the treatment light source 7 and is provided with a transmission window 10 at the center to allow irradiation light from the treatment light source 7 to pass through. In the present embodiment, the transmission window 10 is a hole provided in the patient contact part 9. The transmission window 10 is required only to allow irradiation light to pass through, and the patient contact part 9 may be partially formed of a material that transmits light, such as glass and plastic film.

The observation module 3 includes a camera 11, an illumination light source 12, and a module casing 13. The camera 11 is a member for the patient to grasp the irradiation position and area of the photoirradiation site on the back. As for camera 11, a CCD camera or a CMOS camera can be used. As described later, the image acquired by the camera 11 is displayed on an external monitor through wired or wireless communication. The illumination light source 12 is a member that illuminates the field of observation of the camera 11 to facilitate recognition of the irradiation position and the irradiation area by the camera 11. As for illumination light source 12, a laser, an LED, a halogen lamp, or a xenon lamp can be used. The module casing 13 is a member for holding the camera 11 and the illumination light source 12 and is equipped with an observation module power supply 14 inside for supplying electric power to the camera 11 and the illumination light source 12. As for observation module power supply 14, a primary battery or a secondary battery can be used. Alternatively, electric power may be externally supplied through a cable or the like.

The observation module 3 and the probe fixing unit 1 are connected via a hinge 15. The hinge 15 is a member for moving the observation module 3 relative to the probe insertion part 8 and has one end fixed to the upper end (the end on the opposite side to the patient) of the probe insertion part 8 and the other end fixed to the outer periphery of the observation module 3. FIG. 2 is the arrangement of the observation module 3 and the probe fixing unit 1 when the irradiation probe 2 is not inserted. The observation module 3 has an outer diameter set to be equal to or greater than the outer diameter of the probe insertion part 8 and thus functions as the cap of the probe insertion part 8 in a state in which the irradiation probe 2 is not inserted and the hinge 15 is closed. In the state as in FIG. 2, the observation module 3 is positioned on the top of the probe fixing unit 1, and the camera 11 in the observation module 3 is positioned such that the skin can be observed through the transmission window 10. This configuration enables the patient to visually recognize the marking at the back which is out of sight of the patient. The illumination light source 12 in the observation module 3 can illuminate the skin through the transmission window 10 to make the marking more visible. In this state, the observation module 3 and the camera 11 contained in the observation module 3 are at a position where they interfere with insertion of the irradiation probe 2.

By contrast, the observation module 3 can be moved to the position at which probe insertion is not hindered by opening the hinge 15 when the irradiation probe 2 is inserted into the probe insertion part 8. In the present embodiment, the observation module 3 and the probe fixing unit 1 are connected via the hinge 15. However, the connection part is not necessarily provided between the observation module 3 and the probe fixing unit 1 and they may be detachable from each other.

The fixing belt 4 is a member for fixing the probe fixing unit 1 around the patient's body and attached to the probe fixing unit 1. FIG. 3 is a diagram illustrating the arrangement of an irradiation field 16 of the irradiation light when the irradiation probe 2 is inserted in the probe insertion part 8 and a field of observation 18 of the camera 11 when the irradiation probe 2 is not inserted and the patient skin 17 is observed using the observation module 3. The irradiation probe 2 and the observation module 3 are fixed such that the irradiation light and the field of observation 18 are arranged coaxially toward the patient skin 17. The treatment light source 7 and the camera 11 are thus arranged coaxially, so that the irradiation position and the irradiation area can be grasped accurately. Since the irradiation probe 2 is detachable from the probe fixing unit 1 and positioning can be performed by the lightweight probe fixing unit 1 alone, the patient can easily perform alignment and fixing by himself/ herself even at the back.

Usage of First Embodiment

A specific usage of the present phototherapy device is described with reference to FIG. 4, FIG. 5, and FIG. 6.

FIG. 4 is a diagram illustrating a photoirradiation position of a patient. First of all, the patient's treatment site to be irradiated with light is specified under physician's diagnosis at a hospital or clinic. For example, in LUTS treatment by photoirradiation, the position of sacral foramina to be irradiated with light in the patient's back 19 is located by palpation or X-ray fluoroscopy.

A physician or any other healthcare worker then makes a marking 20 on the specified treatment site. For example, ink or adhesive sheet can be used as the material of the marking 20. The marking 20 is preferably shaped so as to avoid the irradiation area. For example, a hollow circular shape larger than the irradiation area may be employed, although embodiments are not limited thereto.

When the patient thereafter performs photoirradiation at home by himself/herself, the patient fixes the probe fixing unit 1 of the present photoirradiation device in alignment with the marking 20 made at a hospital or clinic.

FIG. 5 is a diagram illustrating the method of placing the probe fixing unit 1 in alignment with the marking 20 on the patient. The patient first turns on the observation module power supply 14 of the observation module 3 and fixes the module at a predetermined position of the probe fixing unit 1 (in the present embodiment, the position with the hinge 15 closed). Next, the probe fixing unit 1 is brought to the back, the state of the back is observed with the observation module 3 attached to the probe fixing unit 1, and then the marking 20 is recognized on a monitor 21. The probe fixing unit 1 is moved such that the marking 20 is at the center of a field of observation 18, and is positioned on the patient skin 17. In this state, a fixing belt 4 is wound around the body and the probe fixing unit 1 is fixed. Subsequently, as illustrated in FIG. 6, the observation module 3 is removed from the probe fixing unit 1 and the irradiation probe 2 is inserted.

Conventionally, when the camera 11 is placed in the probe fixing unit 1, the camera 11 is placed such that the marking 20 is captured by the camera 11 in the appropriately positioned state. If so, the irradiation probe 2 interferes with the camera 11 when being inserted into the probe fixing unit 1. The problem is conspicuous particularly when the camera 11 is arranged such that the optical axis of the camera 11 is present coaxially relative to the optical axis of the treatment light source 7 of the irradiation probe 2 fixed on the probe fixing unit 1 in order to improve the positioning accuracy. In the present phototherapy device, the observation module 3 can move between a first position at which it overlaps with the path of inserting the irradiation probe 2 and a second position at which it does not overlap with the path, so that the marking 20 can be observed from substantially the same position as the irradiation probe 2 is to be fixed, while the irradiation probe 2 does not interfere with the camera 11 when being inserted into the probe fixing unit 1. Accordingly, even when the treatment site is in the back which is out of sight of the patient, and the patient performs photoirradiation by himself/herself, for example, at home, the patient can easily perform alignment and fixing by himself/ herself on the back. This configuration enables photoirradiation accurately aiming at the sacral foramina and consequently provides appropriate treatment. The configuration therefore can be widely utilized as a phototherapy device, for example, for LUTS patients.

Hardware Configuration of Second Embodiment

FIG. 7 and FIG. 8 are diagrams illustrating another embodiment of the present phototherapy device. Since there are many overlaps between the present embodiment and other embodiments, only the features characterizing the present embodiment will be described below and other descriptions of the configuration are omitted. In the present embodiment, the observation module 3 and the probe fixing unit 1 are connected via a rotation shaft 22 parallel to the direction of the center axis of the probe fixing unit 1. The rotation shaft 22 is a member for rotationally moving the observation module 3. When the irradiation probe 2 is not inserted in the probe insertion part 8, as illustrated in FIG. 8, the observation module 3 is positioned such that the patient skin 17 can be observed with the observation module 3 through the transmission window 10, and when the irradiation probe 2 is inserted in the probe insertion part 8, the observation module 3 can be easily moved with a smaller force to a position where it does not interfere with the probe insertion as illustrated in FIG. 7.

Hardware Configuration of Third Embodiment

FIG. 9 and FIG. 10 are diagrams illustrating another embodiment of the present phototherapy device. Since there are many overlaps between the present embodiment and other embodiments, only the features characterizing the present embodiment will be described below and other descriptions of the configuration are omitted. In the present embodiment, as illustrated in FIG. 9, the observation module 3 and the probe fixing unit 1 are connected via a rotation shaft 22 vertical to the direction of the center axis of the probe fixing unit 1. The observation module 3 includes a lever part 23 for rotating the observation module 3 in accordance with the movement of the irradiation probe 2 and an observation part 24 including a camera 11 and an illumination light source 12. The probe fixing unit 1 has a movement groove 25 for moving the observation part 24 to the outside of the probe insertion part 8 when the lever part 23 is pushed by the irradiation probe 2. When the irradiation probe 2 is not inserted in the probe insertion part 8, this structure enables an arrangement such that the patient skin 17 can be observed with the observation part 24 through the transmission window 10. When the irradiation probe 2 is inserted in the probe insertion part 8, as illustrated in FIG. 10, the irradiation probe 2 pushes the lever part 23, so that the observation module 3 accordingly rotates around the rotation shaft 22 and moves out of the probe insertion part 8 through the movement groove 25. Thus, only by inserting the irradiation probe 2 into the probe insertion part 8, the observation module 3 can be easily moved to the position where the observation module 3 does not interfere with the insertion of the irradiation probe 2.

Hardware Configuration of Fourth Embodiment

FIG. 11 is a perspective view illustrating another embodiment of the present phototherapy device. FIG. 12 is a diagram illustrating a support casing 27 cut into halves in the present embodiment. Since there are many overlaps between the present embodiment and other embodiments, only the features characterizing the present embodiment will be described below and other descriptions of the configuration are omitted. In the present embodiment, as illustrated in FIG. 11 and FIG. 12, the observation module 3 includes a camera 11, an illumination light source 12, and a rotational housing 26 and is placed inside the support casing 27 of the probe fixing unit 1. The rotational housing 26 further includes a rotation shaft 22 connecting the probe fixing unit 1 and the observation module 3, and a notch 28. The irradiation probe 2 is provided with a probe protrusion 29 to be fitted in the notch 28. FIG. 13 illustrates a state of the present embodiment when the irradiation probe 2 is not inserted. In this case, the camera 11 and the illumination light source 12 face the patient's skin 17 to enable the patient to grasp the irradiation position and the irradiation area and accurately fix the probe fixing unit 1 at an appropriate position. FIG. 14 illustrates a state of the present embodiment when the irradiation probe 2 is inserted. When the irradiation probe 2 is inserted, the probe protrusion 29 fits in the notch 28 and rotates the rotational housing 26 around the rotation shaft 22. Then, the camera 11 and the illumination light source 12 move from the patient's skin 17 side, and instead the treatment light source 7 equipped in the irradiation probe 2 is positioned in the direction in which the patient's skin 17 can be irradiated with irradiation light. FIG. 15 is a diagram illustrating the arrangement of irradiation light when the irradiation probe 2 is inserted in the probe insertion part 8 and the field of observation 18 of the camera 11 when the irradiation probe 2 is not inserted and the patient's skin 17 is observed with the observation module 3, in the present embodiment. The irradiation probe 2 and the observation module 3 are fixed such that the irradiation field 16 and the field of observation 18 are arranged coaxially toward the patient's skin 17. With such a configuration, the field of observation 18 can be moved only by inserting the irradiation probe 2.

Hardware Configuration of Fifth Embodiment

FIG. 16 is a perspective view illustrating another embodiment of the present phototherapy device. Since there are many overlaps between the present embodiment and other embodiments, only the features characterizing the present embodiment will be described below and other descriptions of the configuration are omitted. In the present embodiment, the observation module 3 is placed on a side surface of the probe fixing unit 1, and an observation mirror 30 is placed in the probe fixing unit 1. The observation mirror 30 is connected to the probe fixing unit 1 via a mirror-moving hinge 31. The irradiation probe 2 is shaped so as to avoid the observation mirror 30 when being inserted. FIG. 17 illustrates a state of the present embodiment when the irradiation probe 2 is not inserted. In this case, the observation mirror 30 extends into the probe fixing unit 1, and the observation mirror 30 is arranged such that the field of observation 18 of the camera 11 in the observation module 3 and light of the illumination light source 12 are directed toward the patient's skin 17 via the observation mirror. In this case, as illustrated in FIG. 18, the observation module 3 and the observation mirror 30 are arranged such that the field of observation 18 reflected by the observation mirror 30 and the irradiation field 16 of irradiation light radiated from the treatment light source 7 in the irradiation probe 2 are arranged coaxially. With such a configuration, when the irradiation probe 2 is not inserted, the field of observation 18 can be observed with the observation mirror 30, and when the irradiation probe 2 is inserted, the observation mirror 30 is moved only by pushing the observation mirror 30, and the irradiation probe 2 can be fixed such that the field of observation 18 of the camera 11 inside the observation module 3 and the irradiation light from the treatment light source 7 are coaxial.

Hardware Configuration of Sixth Embodiment

FIG. 19 is a perspective view illustrating another embodiment of the present phototherapy device. Since there are many overlaps between the present embodiment and other embodiments, only the features characterizing the present embodiment will be described below and other descriptions of the configuration are omitted. In the present embodiment, the observation module 3 has a positioning guide 32. Although FIG. 19 illustrates an example in which the guide 32 is provided in the phototherapy device described in the first embodiment by way of an example, the guide 32 may be provided in the phototherapy device described in the other embodiments. The positioning guide 32 may be provided with a physical marker that can be caught by the camera 11 as illustrated in FIG. 19 or may have the function of being electronically displayed on the monitor 21 as illustrated in FIG. 20. This function enables the patient to easily learn the relationship between the position of the marking 20 and the current position of the probe fixing unit 1 and make alignment more accurately.

Hardware Configuration of Seventh Embodiment

FIG. 21 is a perspective view illustrating another embodiment of the present phototherapy device. Since there are many overlaps between the present embodiment and other embodiments, only the features characterizing the present embodiment will be described below and other descriptions of the configuration are omitted. In the present embodiment, a fine adjustment mechanism 33 is provided between the probe insertion part 8 of the probe fixing unit 1 and the patient contact part 9, wherein the mechanism moves the probe insertion part 8 and the patient contact part 9 relative to each other and can fix them at the position where movement terminates. The fine adjustment mechanism 33 is a member for finely adjusting the positional relationship between the probe insertion part 8 and the patient contact part 9, and can adopt a screw feed mechanism or a spring type moving mechanism. In the present embodiment, it is preferable if the transmission window 10 provided in the patient contact part 9 is larger than the area of the inner periphery of the probe insertion part 8. With the fine adjustment mechanism 33, even when the probe fixing unit 1 is out of alignment with the marking 20 because of body movement and the like after the patient once moves the probe fixing unit 1 and positions it in alignment with the marking 20 on the patient's skin 17 and fixes it using the fixing belt 4, the patient can promptly make fine adjustment by moving the position of the probe insertion part 8 relative to the patient contact part 9 without taking off the fixing belt 4. Although FIG. 21 illustrates an example in which the fine adjustment mechanism 33 is provided in the phototherapy device described in the first embodiment by way of an example, the fine adjustment mechanism 33 may be provided in the phototherapy device described in the other embodiments.

Hardware Configuration of Eighth Embodiment

FIG. 22 is a perspective view illustrating another embodiment of the present phototherapy device. Since there are many overlaps between the present embodiment and other embodiments, only the features characterizing the present embodiment will be described below and other descriptions of the configuration are omitted. In the present embodiment, a flexible medium 34 is provided beneath the patient contact part 9. For example, a resin cushion material or an air cushion may be used as the flexible medium 34. With this configuration, even when the irradiation site is an uneven surface of the patient body as illustrated in FIG. 23, the probe fixing unit 1 can be fitted on the body surface. Thus, even when body movement and the like occur, the probe fixing unit 1 can be securely fixed to the patient's back 19 to enable appropriate radiation. Although FIG. 22 illustrates an example in which the flexible medium 34 is provided in the phototherapy device described in the first embodiment by way of an example, the flexible medium 34 may be provided in the phototherapy device described in the other embodiments.

Hardware Configuration of Ninth Embodiment

FIG. 24 is a perspective view illustrating another embodiment of the present phototherapy device. Since there are many overlaps between the present embodiment and other embodiments, only the features characterizing the present embodiment will be described below and other descriptions of the configuration are omitted. In the present embodiment, the fixing belt 4 is detachable from the probe fixing unit 1. As illustrated in FIG. 25, the fixing belt 4 includes a belt body 35, a belt fixing part 36, a belt attachment part 37, and a through hole 38. The belt fixing part 36 is a member for the patient to fix the belt to the body, and can adopt a hook and loop fastener, an adhesive tape, or a clip can be used. The belt attachment part 37 is a member for allowing the belt to be attached to/detached from the probe fixing unit 1 and can adopt, for example, a configuration of screwing or pinning to the probe fixing unit 1 through holes in the belt. The through hole 38 enables a configuration to appropriately apply the irradiation light radiated from the treatment light source 7 in the irradiation probe 2 to the patient's back 19 without being blocked by the belt body 35. With this configuration, when the belt becomes dirty because of the frequent use of the present phototherapy device, the belt alone can be removed and washed or replaced, and thus the belt can be kept clean.

Hardware Configuration of Tenth Embodiment

FIG. 26 is a perspective view illustrating another embodiment of the present phototherapy device. Since there are many overlaps between the present embodiment and other embodiments, only the features characterizing the present embodiment will be described below and other descriptions of the configuration are omitted. In the present embodiment, two fixing belts 4 are removably attached to the belt attachment part 37 of the probe fixing unit 1. As illustrated in FIG. 27, each of two fixing belts 4 includes a front belt fixing part 39 and a side belt fixing part 40. The belt fixing part 40 is a member for the patient to fix the belt to the body, and can adopt a hook and loop fastener, an adhesive tape, or a clip. In this configuration, the patient first moves the probe fixing unit 1 in alignment with the marking 20 and positions it on the patient skin 17 while keeping the side belt fixing part 40 fixed. After fixing the belt to the body with the front belt fixing parts 39, the patient can further tighten the belt by once releasing the side belt fixing part 40 and then pulling it to surely fix the probe fixing unit 1 to the body.

In the above embodiments, the phototherapy device according to the present invention is used for LUTS treatment by irradiating the position of the sacral foramina of a patient with light. However, the phototherapy device according to the present invention is applicable to treatment of other diseases. For example, the applications include dyschezia treatment, functional dyspepsia treatment, sexual dysfunction treatment, inflammatory bowel treatment, pain relief, nephropathy treatment, rheumatism treatment, sudden deafness treatment, atopic dermatitis treatment, and wound healing acceleration.

In the above embodiments, it is explained that irradiation light is radiated from the irradiation probe toward a living body. However, under the condition in which the treatment site is located at the position which is out of sight of the patient, such as the back, and the device is for the patient to perform energy irradiation by himself/herself at home, the similar effects can be achieved using radiation energy other than laser light. Examples of other applicable radiation energy include electricity, electromagnetic waves (including magnetism, electric waves, light, and low frequency), sound (including ultrasonic wave and soundwave), and heat.

REFERENCE SIGNS LIST

1 Probe fixing unit
2 Irradiation probe
3 Observation module
4 Fixing belt
5 Probe cable
6 Probe casing 7 Treatment light source
8 Probe insertion part
9 Patient contact part
10 Transmission window
11 Camera
12 Irradiation light source
13 Module casing
14 Observation module power supply
15 Hinge
16 Irradiation field
17 Patient's skin
18 Field of observation
19 Patient's back
20 Marking
21 Monitor
22 Rotation shaft
23 Lever part
24 Observation part
25 Movement groove
26 Rotational housing
27 Support casing
28 Notch
29 Probe protrusion
30 Observation mirror
31 Mirror-moving hinge
32 Positioning guide
33 Fine adjustment mechanism
34 Flexible medium
35 Belt body
36 Belt fixing part
37 Belt attachment/detachment part
38 Through hole
39 Front belt fixing part
40 Side belt fixing part

The invention claimed is:

1. A phototherapy device comprising:
an irradiation probe for radiating irradiation light toward an irradiation site on a living body;
a probe fixing unit into which the irradiation probe is insertable and which is fixed on the living body;
an observation module which is placed on the probe fixing unit for observing the irradiation site on the living body; and
a moving means capable of moving the observation module with respect to the probe fixing unit, in a state in which the irradiation probe is not inserted into the probe fixing unit for observation of the irradiation site, to a space where the irradiation probe is to be placed in the probe fixing unit for radiating the irradiation light toward the irradiation site.

2. The phototherapy device according to claim 1, wherein an irradiation field of the irradiation light from the irradiation probe and a field of the observation of the observation module are coaxial with respect to the irradiation site on the living body.

3. The phototherapy device according to claim 1, wherein the moving means is a hinge formed between the probe fixing unit and the observation module.

4. The phototherapy device according to claim 1, wherein the moving means is a rotation shaft formed between the probe fixing unit and the observation module.

5. The phototherapy device according to claim 4, wherein the moving means further comprises a lever which causes the observation module to rotate by insertion of the irradiation probe into the probe fixing unit and move out from the space in which the observation module was positioned for the observation of the irradiation site.

6. The phototherapy device according to claim 1, wherein the observation module comprises an observation mirror, and
the moving means is capable of moving the observation mirror into the space where the irradiation probe is to be placed in the probe fixing unit.

7. The phototherapy device according to claim 1, wherein the observation module is provided with a positioning guide.

8. The phototherapy device according to claim 1, wherein the probe fixing unit is provided with an adjustment mechanism.

9. The phototherapy device according to claim 1, wherein a flexible medium is formed at a part of the probe fixing unit.

10. The phototherapy device according to claim 1, wherein the probe fixing unit is provided with a removable fixing belt.

11. The phototherapy device according to claim 10, wherein the removable fixing belt is provided with two belts each equipped with a front belt fixing part and a side belt fixing part.

12. The phototherapy device according to claim 1, wherein the moving means comprises one of a hinge or a rotation shaft.

* * * * *